(12) United States Patent
Rizzo et al.

(10) Patent No.: US 10,845,337 B2
(45) Date of Patent: Nov. 24, 2020

(54) METHOD FOR CHARACTERIZING POLYSACCHARIDES

(71) Applicants: ECOLE POLYTECHNIQUE FEDERALE DE LAUSANNE (EPFL), Lausanne (CH); INDIANA UNIVERSITY RESEARCH AND TECHNOLOGY CORPORATION, Indianapolis, IN (US)

(72) Inventors: Thomas Rizzo, Denens (CH); Chiara Masellis, Munich (DE); Michael Zachary Kamrath, Morges (CH); David Clemmer, Bloomington, IN (US); Neelam Khanal, Bloomington, IN (US)

(73) Assignees: ECOLE POLYTECHNIQUE FEDERALE DE LAUSANNE (EPFL), Lausanne (CH); INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 16/328,995

(22) PCT Filed: Aug. 29, 2017

(86) PCT No.: PCT/IB2017/055175
§ 371 (c)(1),
(2) Date: Feb. 27, 2019

(87) PCT Pub. No.: WO2018/042325
PCT Pub. Date: Mar. 8, 2018

(65) Prior Publication Data
US 2019/0204272 A1  Jul. 4, 2019

(30) Foreign Application Priority Data
Aug. 29, 2016 (WO) ................. PCT/IB2016/055159

(51) Int. Cl.
*H01J 49/00* (2006.01)
*G01N 27/62* (2006.01)
(Continued)

(52) U.S. Cl.
CPC ........ *G01N 27/622* (2013.01); *B01J 19/0013* (2013.01); *B01J 19/121* (2013.01);
(Continued)

(58) Field of Classification Search
CPC .... H01J 49/40; H01J 49/0031; G01N 27/622; G01N 21/35; B01J 19/0013; B01J 19/121
See application file for complete search history.

(56) References Cited

U.S. PATENT DOCUMENTS 8,835,839 B1 9/2014 Anderson et al.
10,522,337 B2 * 12/2019 Rizzo ..................... G01N 1/28
(Continued)

FOREIGN PATENT DOCUMENTS

| GB | 2531336 | 4/2016 |
|---|---|---|
| WO | 98/56029 | 12/1998 |
| WO | 2012/051138 | 4/2012 |

OTHER PUBLICATIONS

Masson, Antoine, et al. "Infrared Spectroscopy of Mobility-Selected H+-Gly-Pro-Gly-Gly (GPGG)." Journal of the American Society for Mass Spectrometry 26.9 (Jun. 2015): 1444-1454 (Year: 2015).*
(Continued)

*Primary Examiner* — Wyatt A Stoffa
(74) *Attorney, Agent, or Firm* — Nixon & Vanderhye P.C.

(57) ABSTRACT

A method for a structural characterization of polysaccharides, comprising steps of characterizing a polysaccharide by physical measurements comprising a determination of a mass of the polysaccharide by means of mass spectrometry, a further determination of a rotationally averaged cross section of the polysaccharide by means of ion mobility
(Continued)

spectrometry, and an infrared spectrum of the polysaccharide by means of cryogenic, messenger-tagging IR spectroscopy.

8 Claims, 5 Drawing Sheets

(51) Int. Cl.
  *H01J 49/40* (2006.01)
  *G01N 21/35* (2014.01)
  *B01J 19/00* (2006.01)
  *B01J 19/12* (2006.01)

(52) U.S. Cl.
  CPC .......... *G01N 21/35* (2013.01); *H01J 49/0031* (2013.01); *H01J 49/40* (2013.01)

(56) References Cited

U.S. PATENT DOCUMENTS

| | | | |
|---|---|---|---|
| 2015/0129761 A1* | 5/2015 | Johnson | G01N 21/35 250/282 |
| 2015/0168318 A1* | 6/2015 | Beckman | G01N 23/2055 250/307 |
| 2016/0071715 A1 | 3/2016 | Anderson et al. | |
| 2018/0246062 A1* | 8/2018 | Hofmann | G01N 33/6848 |
| 2019/0180997 A1* | 6/2019 | Rizzo | H01J 49/0031 |
| 2019/0204272 A1 | 7/2019 | Rizzo et al. | |
| 2019/0206516 A1* | 7/2019 | Compagnon | C07H 13/02 |

OTHER PUBLICATIONS

Masson, Antoine, et al. "Infrared Spectroscopy of Mobility-Selected H+-Gly-Pro-Gly-Gly (GPGG)." Journal of the American Society for Mass Spectrometry 26.9 (Jun. 2015): 1444-1454 (Year: 2015).*
International Search Report for PCT/IB2017/055175, dated Jan. 11, 2018, 4 pages.
Written Opinion of the ISA for PCT/IB2017/055175, dated Jan. 11, 2018, 6 pages.
Antoine et al., "Infrared Spectroscopy of Mobility-Selected H+-Gly-Pro-Gly-Gly (GPGG)", Journal of the American Society for Mass Spectrometry, vol. 26, No. 9, Jun. 20, 2015, pp. 1444-1454.
Gaye et al., "Investigating carbohydrate isomers by IMS-CID-IMS-MS: precursor and fragment ion cross-sections", Analyst, vol. 140, No. 20, Jan. 1, 2015, pp. 6922-6932.
Stefan et al. "Differentiation of Closely Related Isomers: Application of Data Mining Techniques in Conjunction with Variable Wavelength Infrared Multiple Photon Dissociation Mass Spectrometry for Identification of Glucose-Containing Disaccharide Ions", Analytical Chemistry, vol. 83, No. 22, Nov. 15, 2011, pp. 8468-8476.

* cited by examiner

METHOD FOR CHARACTERIZING POLYSACCHARIDES

This application is the U.S. national phase of International Application No. PCT/IB2017/055175 filed 29 Aug. 2017, which designated the U.S. and claims priority to PCT/IB2016/055159 filed 29 Aug. 2016, the entire contents of each of which are hereby incorporated by reference.

TECHNICAL FIELD

The invention is in the field of polysaccharides, and more particularly the characterization of such polysaccharides.

BACKGROUND

The structural characterization of bioactive polysaccharides, or glycans, is one of the cornerstones of glycobiology. Glycans are biopolymers formed from monosaccharides linked by glycosidic bonds and are ubiquitous in cells and tissues. They are involved in cell adhesion and movement, and they influence gene expression. The immune system is able to recognize specific glycan sequences on bacteria and viruses, triggering an immune response. As such, glycans are important components of therapeutic drugs to help treat chronic and infectious diseases and can serve as biomarkers to detect diseases such as cancer. In order to understand the detailed role that glycans play in biological systems and to generate synthetic analogs, the molecular structure of natural polysaccharides must be characterized in detail. This is an extremely challenging task. While mass spectrometric (MS) sequencing is well suited to characterizing the structure of proteins and nucleic acids, the particular challenges posed by glycans limits their analysis by traditional MS techniques.

The difficulty in determining polysaccharide structure arises from the nature of the monomer units that comprise them and the way that they are attached to each other, leading to several sources of complication:
(1) As opposed to proteins and nucleic acids, which are linear sequences formed from a pool of monomers of different mass, many of the monosaccharide units that constitute glycans have the same mass, differing only by the stereochemistry of chiral centers, and thus it is impossible to distinguish by traditional MS/MS techniques. This makes determining the monosaccharide content particularly challenging.
(2) While the monomer units of both proteins and nucleic acids have single, unique points of attachment, the glycosidic bond between monosaccharides can have a variety of attachment points. This has two implications for structure determination.
   a. In cases where there is only a single attachment point between two monomers, the fact that these points are not unique leads to the possibility of having different regioisomers. This means that molecules of the same mass, same monosaccharide content and same sequence can have a different structure and different properties.
   b. The existence of multiple attachment points leads to the possibility of branched structures, which can have the same mass as linear structures of the same monosaccharide content
(3) Because the attachment point between monosaccharides, called the glycosidic bond, is a stereogenic center, each linkage can exist as both α and β anomers, which have the same mass but different stereochemistry.
(4) Because of the large number of hydroxyl groups, polysaccharides can be functionalized at many different locations (e.g., by phosphate or sulfates). Polysaccharides with different functionalization sites have the same mass and cannot easily be distinguished by mass spectrometry.

A problem addressed by the present invention is to be able to take a polysaccharide of unknown origin and determine: (a) its monosaccharide content; (b) it sequence; (c) the attachment point of each glycosidic bond, including any branching; (d) the stereochemistry of each glycosidic bond (i.e., α or β anomers); and (e) the identity and position of any functional groups.

SUMMARY OF INVENTION

In a first aspect, the invention provides a method for a structural characterization of polysaccharides, comprising steps of characterizing a polysaccharide by physical measurements comprising a determination of a mass of the polysaccharide by means of mass spectrometry, a further determination of a rotationally averaged cross section of the polysaccharide by means of ion mobility spectrometry, and an infrared spectrum of the polysaccharide by means of cryogenic, messenger-tagging IR spectroscopy.

In a preferred embodiment, the method further comprises applying the step of characterizing to an unknown sample of polysaccharides, and determine its structure by comparison with a previously prepared database of measurements for a determined number of polysaccharides.

In a further preferred embodiment, the step of characterizing further comprises providing a liquid sample of the polysaccharides, and volatilizing the liquid sample by electrospray ionization and injecting the volatilized liquid sample as a packet into a drift-tube used for the ion mobility spectrometry.

In a further preferred embodiment, the ion mobility spectroscopy comprises determining a drift time of the polysaccharide through the drift-tube at a constant pressure of a bath gas for the determination of the rotationally averaged cross section.

In a further preferred embodiment, the determination of the infrared spectrum further comprises selecting polysaccharides that have a particular drift time and mass; injecting the selected polysaccharides into a cryogenic ion trap, in which they are confined, collisionally cooled and tagged by at least one messenger molecule; irradiating the tagged polysaccharides with an infrared laser to excite them vibrationally; and injecting the irradiated polysaccharides into a time-of-flight mass spectrometer configured to detect a number of polysaccharides at masses of both the tagged and untagged polysaccharides.

In a further preferred embodiment, the step of determination of the infrared spectrum further comprises, for successive measurements on the selected polysaccharides, varying a laser frequency; and plotting a depletion in the number of tagged polysaccharides as a function of the laser frequency, thereby obtaining a vibrational spectrum of the selected polysaccharide.

In a second aspect, the invention provides a device for structural characterization of bioactive polysaccharides, comprising an electrospray ion source; an Ion Mobility Spectrometry drift tube; a cryogenic ion trap; and a time-of flight mass spectrometer.

BRIEF DESCRIPTION OF THE DRAWINGS

The invention will be better understood through the detailed description of preferred embodiments and in reference to the drawings, wherein FIG. 1a contains a schematic of a hybrid machine combining Ion Mobility Spectrometry (IMS) with a cold ion trap for spectroscopic studies according to the invention;

FIG. 1b shows a planar, cryogenic ion trap that couples directly to a reflection time-of-flight mass spectrometer (TOFMs), as shown in FIG. 1a;

DETAILED DESCRIPTION OF PREFERRED EMBODIMENTS OF THE INVENTION

A solution to the problem to be solved is to characterize each polysaccharide by three physical measurements:

(1) its mass, determined using mass spectrometry;
(2) its rotationally averaged cross section, determined by ion mobility spectrometry; and
(3) its infrared spectrum, using cryogenic, messenger-tagging spectroscopy.

Figure 1A:
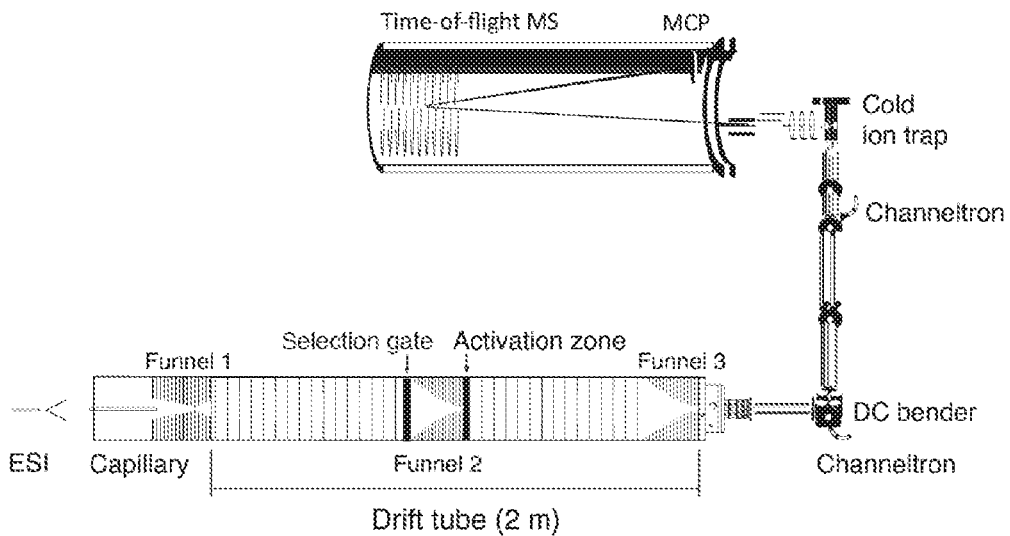
Figure 1B:
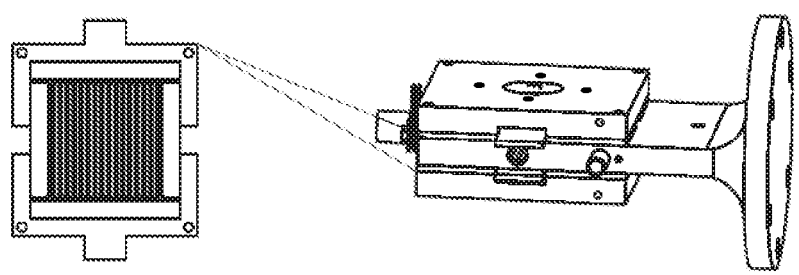

Toward this end, the invention provides a single instrument to measure all of the above quantities (mass, average cross section, and infrared spectrum). As shown in FIG. 1a, the single instrument combines an electrospray ion source with an Ion Mobility Spectrometry (IMS) drift-tube and a cryogenic ion trap. Liquid samples are volatilized by electrospray ionization and injected as a packet into the ion mobility spectrometry drift-tube. From the drift time through the drift-tube at a constant pressure of a bath gas (which is typically, but not exclusively helium) we determine the rotationally averaged cross section. Upon exit of the drift-tube, the ions are bent 90° and passed through a quadrupole mass filter, which selects their mass. Ions of a particular drift time and mass are then injected into the cryogenic ion trap, in which they are confined and collisionally cooled to ~15 K and tagged by one or more messenger molecules, which is typically, but not exclusively, hydrogen, deuterium, or nitrogen.

Figure 2:
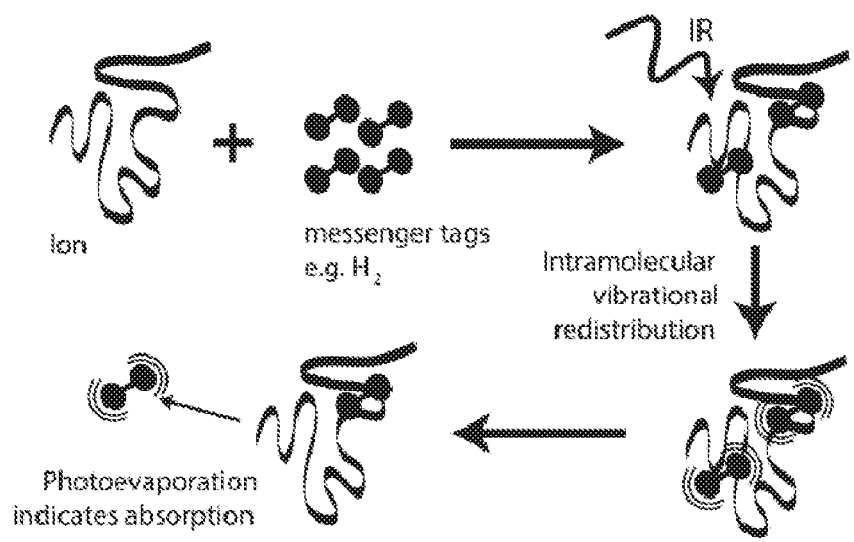
FIG. 2 contains a schematic of the messenger tagging technique for measuring vibrational spectra of cold ions according to the invention.

Once the polysaccharide ions are cooled, trapped and tagged, we pass an infrared laser through the ion packet to excite them vibrationally. If one of the tagged ions absorbs an infrared photon, the energy from that photon will be rapidly redistributed among all of the vibrational modes of the molecule and thus heat it up, leading to evaporation of one or more of the tags. This process is shown schematically in FIG. 2.

After irradiation with the IR laser pulse, the ions are injected into a time-of-flight (TOF) mass spectrometer (FIG. 1a), which detects the number of ions at the masses of both the tagged and untagged ions. This process is repeated with subsequent packets of ions while the laser frequency is scanned. Plotting the depletion in the number of tagged ions as a function of the laser frequency (or wavenumber) produces a vibrational spectrum of the polysaccharide. As shown below, this spectrum provides a unique fingerprint of the molecule that is sensitive to the monosaccharide content, sequence, attachment points and stereochemistry of the glycosidic linkages, and the presence (and location) of different functional groups.

For convenience and as an example, a protocol for implementing the invention is to produce the ions in the form of complexes with sodium cation in the gas phase.

Figure 7:
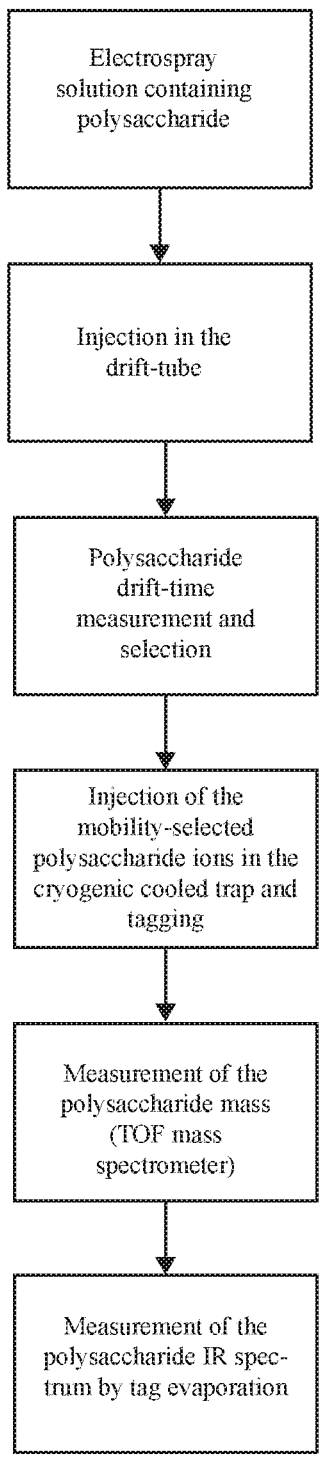
FIG. 7 contains a flowchart of the method according to an example embodiment of the invention.

Referring now to FIG. 7, this illustrates an example embodiment of the method for the structural characterization of polysaccharides according to the invention. More precisely it shows the following sequence of steps:

electrospray the solution containing polysaccharides;
injecting the electrosprayed solution in the drift tube;
performing a polysaccharide drift-time measurement and selection;
injection of the mobility-selected polysaccharide ions in the cryogenic cooled trap and tagging;
measurement of the polysaccharide mass by TOF mass spectrometry; and
measurement of the polysaccharide IR spectrum by tag evaporation.

In a preferred optional embodiment, by taking different polysaccharides of known structure, we may measure the mass, the rotationally averaged cross section, and the infrared spectrum and create a polysaccharide database as reference for subsequent use. We subsequently take an unknown sample, either a single component or a mixture, and determine its composition by comparison with this database.

Experimental Results

The inventors performed experiments on a number of disaccharides to prove the principle that the combination of mass, cross section (from the drift time) and infrared spectra can distinguish the monomeric content, the sequence, and the attachment points and stereochemistry of the glycosidic linkage. For the limited cases that we have tried thus far, the infrared spectrum together with the mass represents a sufficiently distinct fingerprint that the cross section (i.e., drift time) is not needed to distinguish them. Moreover, polysaccharides of a given size (i.e, monomer, dirtier), have similar cross sections. For more complex polysaccharides, particularly in mixtures, all three pieces of information will be needed for unique identification.

It is demonstrated below that the invention allows to easily distinguish the subtle differences between polysaccharides, which is difficult to do by mass spectrometry or other techniques.

Monosaccharide Content

Figure 3:
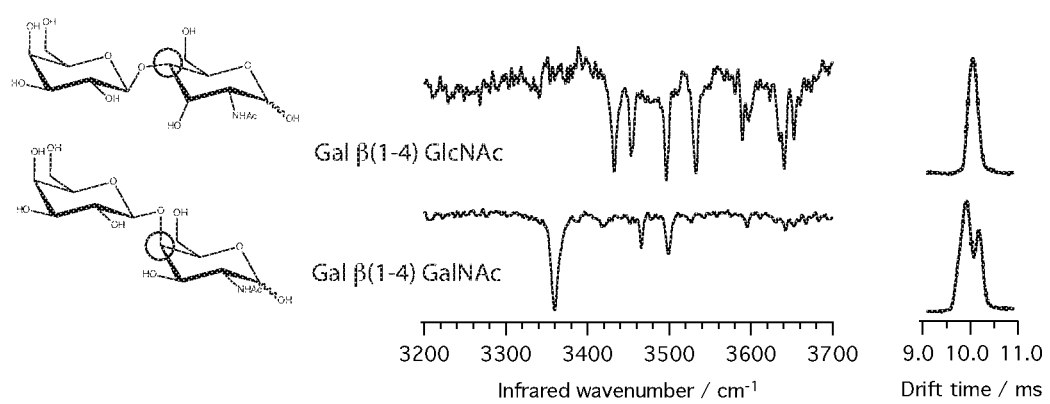
FIG. 3 contains infrared fingerprint spectra and drift-time distributions of two isomeric disaccharides, wherein the two molecules differ only by the orientation of a single stereogenic center, as highlighted by the circles.

FIG. 3 compares the infrared spectra of two isomeric disaccharides, galactose $\beta$ (1-4) N-acetyl-glucosamine and galactose $\beta$ (1-4) N-acetyl-galactosamine. These disaccharides have the same mass, the same stereochemistry of the glycosidic bond, same attachment point but differ in the monosaccharide content, which amounts to a difference in the orientation of a single stereogenic center in the molecule.

Stereochemistry of Glycosidic Linkage

Figure 4:
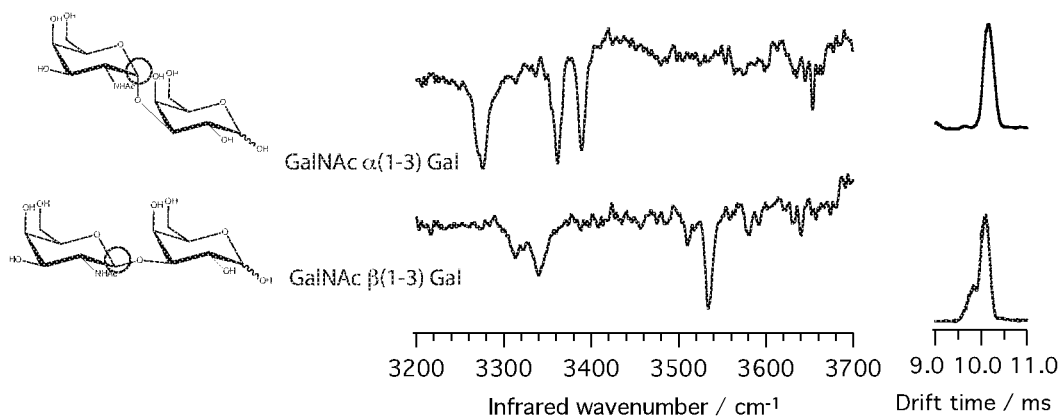
FIG. 4 contains infrared fingerprint spectra and drift-time distributions of two isomeric disaccharides that differ only in the stereochemistry of the glycosidic bond ($\alpha$ vs $\beta$), as highlighted by the circles.

FIG. 4 compares the infrared spectra of two isomeric disaccharides that have the same monosaccharide content, same attachment point but differ simply in the stereochemistry of the glycosidic bond.

Glycosidic Bond Attachment Point

Figure 5:
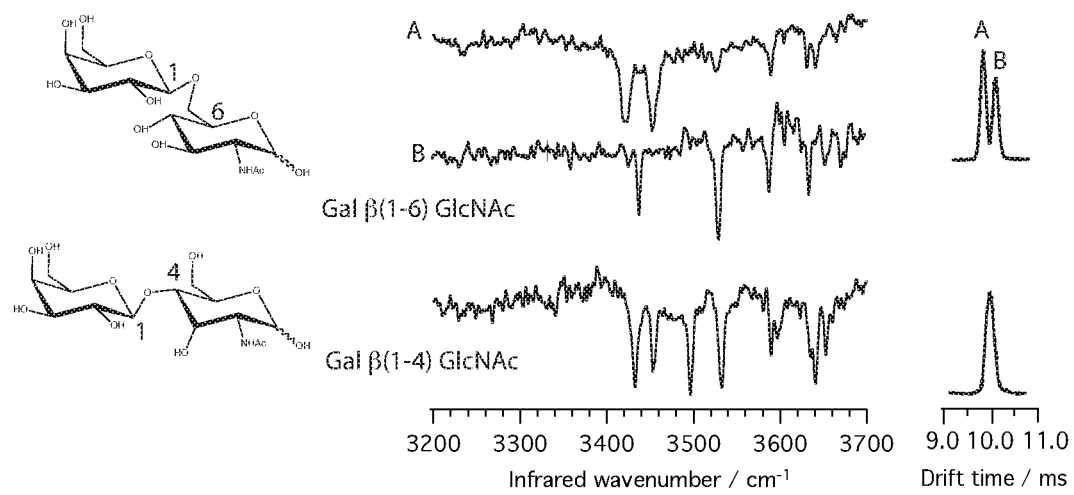
FIG. 5 contains infrared fingerprint spectra and drift-time distributions of two isomeric disaccharides that differ only in the attachment point of the glycosidic bond (1-6 vs 1-4)

FIG. 5 compares two isomeric disaccharides that have the same monosaccharide content, same stereochemistry of the glycosidic bond but differ in their point of attachment.

Sequence Order

Figure 6:
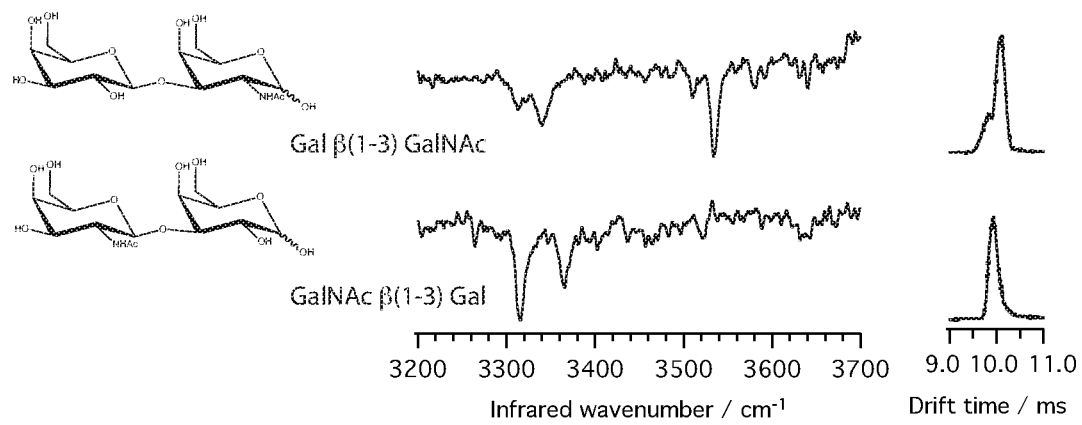
FIG. 6 contains infrared fingerprint spectra and drift-time distributions of two isomeric disaccharides that differ only in their sequence order.

FIG. 6 shows the spectra of two isomeric disaccharides that have the same monosaccharide content, same stereochemistry of the glycosidic bond (both β), same attachment point but differ only in the order of the sequence.

In all these cases, one sees that the infrared spectroscopic fingerprint is unique to each of the disaccharides tested. In some cases, the drift times (and hence the cross sections) are also different, although they all fall in a similar range and often overlap. This is because we are comparing unbranched molecules of a similar size. The cross section will differ more significantly when comparing linear and branched species, for example.

Addressable Market Segments

The present invention is of interest for example both to the medical/pharmaceutical industry as well as to companies that produce analytical instruments.

Advantages Compared to the Existing Technologies on the Market

At least certain advantages of the invention compared to mass-spectrometric approaches are clearly addressed herein above. Ion mobility has also been used to identify polysaccharides, however as may be seen above, for species of similar size, the cross sections determined by their drift time do not widely vary and could not be used as a unique identifier.

SUMMARY

In summary, the present invention makes a new combination with new synergies of techniques and instruments normally applied in molecular physics to investigate the intrinsic structure of biological molecules in the gas-phase. By using a combination of ion mobility and cryogenic messenger-tagging spectroscopy, the invention enables the construction of a database of collisional cross sections and spectroscopic fingerprints to allow the identification of polysaccharides. Sequence identification of the biopolymers is an important task that cannot be addressed using the currently available mass spectrometry techniques, since polysaccharides are made of isomeric building blocks. Ion mobility, in conjunction with spectroscopy, should be able to uniquely characterize polysaccharides in order to allow their identification in samples of biological origin.

The invention claimed is:

1. A method for structural characterization of an unknown polysaccharide, the method comprising the steps of:
    determining a mass of the unknown polysaccharide by mass spectrometry;
    determining a rotationally averaged cross section of the unknown polysaccharide by ion mobility spectrometry;
    determining an infrared spectrum of the unknown polysaccharide by cryogenic, messenger-tagging IR spectroscopy; and
    determining a plurality of features of the unknown polysaccharide including at least one of monosaccharide content, sequence, attachment points and stereochemistry of glycosidic linkages, presence of different functional groups, and location of different functional groups, based on the determined mass, the determined rotationally averaged cross-section, and the determined infrared spectrum of the unknown polysaccharide.

2. The method of claim 1, wherein the method further comprises:
    comparing at least one of the mass, the rotationally averaged cross section, and the infrared spectrum with a previously prepared database of measurements for a determined number of polysaccharides.

3. The method of claim 1, further comprising the steps:
    providing a liquid sample of the unknown polysaccharide; and
    volatilizing the liquid sample by electrospray ionization and injecting the volatilized liquid sample as a packet into a drift-tube used for the ion mobility spectrometry.

4. The method of claim 3, wherein the step of determining the rotationally averaged cross section further comprises the step of:
    determining a drift time of the polysaccharide through the drift-tube at a constant pressure of a bath gas for the determination of the rotationally averaged cross section.

5. The method according to claim 3, wherein the step of determining the infrared spectrum further comprises:
    selecting polysaccharides from a plurality of the unknown polysaccharide that have a particular drift time and mass;
    injecting the selected polysaccharides into a cryogenic ion trap, in which the selected polysaccharides are confined, collisionally cooled and tagged by at least one messenger molecule;
    irradiating the tagged polysaccharides with an infrared laser to excite them vibrationally; and
    injecting the irradiated polysaccharides into a time-of-flight mass spectrometer detect a number of polysaccharides at masses of both the tagged and untagged polysaccharides.

6. The method of claim 5, wherein the step of determining the infrared spectrum further comprises, for successive measurements on the selected polysaccharides,
    varying a laser frequency; and
    plotting a depletion in the number of tagged polysaccharides as a function of the laser frequency to obtain a vibrational spectrum of the selected polysaccharide.

7. The method of claim 1, wherein the mass spectrometry includes a time-of-flight mass spectrometer.

8. The method of claim 1, wherein the method further comprises:
    determining a monomeric content, a sequence, and attachment points and stereochemistry of a glycosidic linkage of the unknown polysaccharide based on the determined mass, rotationally averaged cross section, and infrared spectrum.

* * * * *